(12) United States Patent
Orihashi et al.

(10) Patent No.: US 7,816,399 B2
(45) Date of Patent: Oct. 19, 2010

(54) MEDICINES AND MEDICINAL KITS

(75) Inventors: Masahiro Orihashi, Toyama (JP); Junpei Koike, Toyama (JP); Kanako Masuda, Toyama (JP)

(73) Assignees: Teika Pharmaceutical Co., Ltd., Toyama-shi (JP); Kowa Company Ltd., Nagoya-shi (JP)

( * ) Notice: Subject to any disclaimer, the term of this patent is extended or adjusted under 35 U.S.C. 154(b) by 1292 days.

(21) Appl. No.: 10/475,270

(22) PCT Filed: Apr. 2, 2002

(86) PCT No.: PCT/JP02/03292

§ 371 (c)(1),
(2), (4) Date: Oct. 20, 2003

(87) PCT Pub. No.: WO02/085372

PCT Pub. Date: Oct. 31, 2002

(65) Prior Publication Data

US 2004/0171681 A1 Sep. 2, 2004

(30) Foreign Application Priority Data

Apr. 19, 2001 (JP) ............................. 2001121295

(51) Int. Cl.
*A61K 31/35* (2006.01)
*A61K 31/215* (2006.01)
*A61K 31/19* (2006.01)

(52) U.S. Cl. .................. 514/456; 514/530; 514/573

(58) Field of Classification Search ............... 514/530, 514/573, 456, 912, 913
See application file for complete search history.

(56) References Cited

FOREIGN PATENT DOCUMENTS

| JP | 11-171764 | 6/1999 |
|----|-----------|--------|
| JP | 11-500122 | 6/1999 |
| JP | 11-189537 | 7/1999 |
| JP | 2001-81048 | 3/2001 |
| WO | 00/38689 | 7/2000 |

OTHER PUBLICATIONS

Medline Abstarct 07174609, 1996. Masuda.*

Okumura T. et al., Canine retinal arterial and arteriolar dilation Induced by nipradilol, a possible glaucoma therapeutic, Pharmacology, 1996, vol. 53, No. 5, pp. 302 to 310.
Albach C. et al, Uber Die Drucksenkende Wirkung Von Latanoprost 0, 005 % Klinische Monatsblatter fur Augenheilkunde, 1998, vol. 212. No. 5, pp. 268 to 269.
Drago Filippo et al., Latanoprost exerts neuroprotective activity in vitro and viro, Experimental Eye Research. Apr. 2001 vol. 72, No. 4, pp. 479 to 486 & Databae CAPLUS on STN, American Chemical Society (ACS), (Columbus, OH, USA). DN 135:71229.
Okumura T., et al., "Canine retinal arterial and arteriolar dilatation induced by nipradilol, a possible glaucoma therapeutic", Pharmacology, vol. 53, No. 5, pp. 302-310 1996.
Albach C., et al., Über Die Drucksenkende Wirkung Von Latanoprost 0,005%, Klinische Monatsblatter Fur Augenheilkunde, vol. 212, No. 5, pp. 268-269 1998.
Drago Filippo, et al., "Latanoprost exerts neuroprotective activity in vitro and in vivo", Experimental Eye Research, vol. 72, No. 4, pp. 479-486 2001.
Elke Lütjen-Drecoll, et al., "Morphological Study of the Anterior Segment of Cynomolgus Monkey Eyes Following Treatment with Prostaglandin $F_2$", Exp. Eye Res. vol. 47, pp. 761-769 1988.
Cameron Millar, et al., Investigative Ophthalmology & Visual Science, vol. 36, No. 12, pp. 2461-2465 1995.
Sardar Y.K. Yousufzai, et al., Exp. Eye Res. vol. 63, pp. 305-310, 1996.
Scott A. Waldman, et al., The Journal of Biological Chemistry, vol. 259, No. 23, pp. 14332-14334 1984.
James A. Nathanson, et al., European Journal of Pharmacology, vol. 147, pp. 155-156 1988.
Daniela Salvemini, et al., Proc. Natl. Acad. Sci. USA, vol. 90, pp. 7240-7244 1993.
Furchtgott, Robert F., et al., "The obligatory role of endothelial cells in the relaxation of arterial smooth muscle by acetylcholine", *Nature*, vol. 288, Nov. 27, 1980, pp. 373-376.
Ignarro, Louis J., et al., "Endothelium-derived relaxing factor produced and released from artery and vein is nitric oxide", *Proceedings of the National Academy of Sciences USA*, vol. 84, Dec. 1987, pp. 9265-9269 (Medical Sciences).
Murad, Ferid, et al., "Properties and Regulation of Guanylate Cyclase and Some Proposed Functions for Cyclic GMP", *Advances in Cyclic Nucleotide Research*, vol. 11 (edited by P. Greengard and G.A. Robison), Raven Press, New York, 1979, pp. 175-204.

* cited by examiner

*Primary Examiner*—Zohreh A Fay
(74) *Attorney, Agent, or Firm*—Oblon, Spivak, McClelland, Maier & Neustadt, L.L.P.

(57) ABSTRACT

It is intended to provide medicines having a higher ocular tension-lowering effect on ocular hypertension and glaucoma. Because of showing an excellent effect of lowering ocular tension, medicines comprising a combination of a prostaglandin compound with an NO-donating compound are useful in treating ocular hypertension and glaucoma.

10 Claims, No Drawings

MEDICINES AND MEDICINAL KITS

TECHNICAL FIELD

The present invention relates to a medicine comprising a mixture of a prostaglandin compound and a nitric oxide (hereinafter referred to as "NO") donating compound that is effective in the treatment of ocular hypertension and glaucoma.

BACKGROUND ART

Presently, eye drop solutions and internal medicines are principally used for reducing ocular tension in the treatment of ocular hypertension and glaucoma. As examples of eye drop solutions, β-blockers such as timolol maleate, carteolol hydrochloride, befunolol hydrochloride, and betaxolol hydrochloride, sympathetic nerve stimulants such as epinephrine and dipivefrine hydrochloride, parasympathetic nerve stimulants such as pilocarpine hydrochloride and carbachol, α-blockers such as bunazosin, αβ-blockers such as nipradilol, and prostaglandin derivatives such as isopropyl unoprostone and latanoprost can be given. As examples of internal medicines, carbonic anhydrase inhibitors such as acetazolamide, methazolamide, and diclofenamide can be given.

In many cases, the use of only one of these medicines cannot sufficiently control ocular tension. Therefore, the combined use of two or more of these medicines has increased. However, there are cases where the combined use of these medicines does not significantly reduce ocular tension, thereby making the selection of these medicines very difficult.

Accordingly, an object of the present invention is to provide a medicine that significantly reduces ocular tension resulting from ocular hypertension and glaucoma, in particular, a medicine that effectively reduces ocular tension in cases where the combined use of conventional medicines is not effective.

DISCLOSURE OF THE INVENTION

To achieve the above object, the present inventors have conducted extensive research of a medicine comprising a prostaglandin compound and a NO-donating compound.

Of the above medicines, prostaglandin compounds are already known to be effective in reducing ocular tension when used alone. However, the action mechanism of this effect has not yet been fully understood. It is commonly believed that this effect is due to the increased uveoscleral flow rate and there are several opinions regarding the reason. One opinion is that prostaglandin $F_2\alpha$ causes secretion of MMP. MMP degrades the extracellular matrix of the smooth muscle fibers of the ciliary body (uveoscleral outflow pathway) thereby decreasing outflow resistance and increasing outflow (Lutjen-Drecoll E. and Tamm E., Exp. Eye. Res 47, 761-769, 1988). Another opinion is that the smooth muscle fibers of the ciliary body become relaxed and the cell spacing expands thereby decreasing outflow resistance and increasing outflow (Poyer J F., Inv. Opht. Vis. Sci. 36, 2461-2465, 1995).

The inventors of the present invention paid particular attention to the following reports on prostaglandin. As a result of combining a prostaglandin compound (a derivative of prostaglandin $F_2\alpha$. in particular) with a prostaglandin receptor, phospholipase $A_2$ is stimulated, thereby causing arachidonic acid to be produced and released from the biomembrane phospholipid. This arachidonic acid is converted into prostaglandin $G_2$ by the action of cyclooxygenase then converted into various types of endogenic prostaglandin. In this instance, prostaglandin $E_2$ and prostaglandin $F_2\alpha$ are produced and cause the ciliary muscle to become relaxed thereby increasing the uveoscleral flow rate, and as a result, the ocular tension is reduced (Y. K. Sardar, Exp. Eye. Res. 63, 305, 1996 and the like).

The ocular tension reducing effect of NO donating compounds has already been known in the art. The nitric oxide released by the NO donating compound activates the guanylate cyclase, which increases the amount of cyclic GMP (S. A. Waldman et al, J. Biol. Chem 259, 14332, 1984), and results in reduced ocular tension (J. A. Nathanson Eur. J. Pharmacol. 147, 155, 1988).

In general, the combination of several components effective in reducing ocular tension does not greatly improve the overall effect. However, the inventors of the present invention conducted research based on the assumption that a mixture of a prostaglandin compound and an NO donating compound could significantly reduce ocular tension, wherein the nitric oxide released by the NO donating compound not only activates guanylate cyclase but also activates cycloxygenase (D. Salvemini, et al, Proc. Natl. Acad. Sci. USA 90, 7240, 1993) thereby enhancing the conversion of arachidonic acid in the ocular tension reducing mechanism of the prostaglandin compound. As a result, the inventors have discovered that this combination is in fact highly effective in reducing ocular tension, thereby completing the present invention.

Accordingly, the present invention provides a medicine comprising a prostaglandin compound and an NO donating compound.

The present invention also provides a method for treating and/or preventing ocular hypertension or glaucoma using the above medicine.

Since ocular hypertension and glaucoma can be very difficult to treat, there are many cases where these disorders cannot be completely cured using conventional medicines for reducing ocular tension. Experimented use of various combinations of these medicines, which resulted in either no improvement or only a slight improvement in effect, could not achieve a significant improvement in the treatment of these disorders.

In the medicine of the present invention comprising the combination of a prostaglandin compound and an NO donating compound, the nitric oxide is released from the NO donating compound and enhances the conversion of the arachidonic acid in the ocular tension reducing mechanism of the prostaglandin compound, thereby exhibiting a synergistic effect of the two compounds of significantly increasing the ocular tension reducing effect. Thus, the medicine is not only effective in regular ocular hypertension and glaucoma patients but is also effective in those patients wherein the combined use of several conventional medicines does not significantly reduce ocular tension.

DETAILED DESCRIPTION OF THE PREFERRED EMBODIMENT

As the prostaglandin compound used in the medicine of the present invention, all pharmaceutically acceptable prostaglandin compounds, derivatives, and analogues thereof can be given, wherein the derivatives include pharmaceutically acceptable esters and salts thereof.

As examples of the prostaglandin compound, naturally occurring prostaglandins such as prostagladin (hereinafter referred to as "PG") $D_1$, $PGE_1$, $PGE_2$, $PGE_3$, $PGF_1\alpha$, $PGF_2\alpha$, $PGF_3\alpha$, $PGG_2$, $PGH_2$, $PGI_2$, and $PGI_3$, thromboxane $A_2$, latanoprost, isopropyl unoprostone, $PGF_2\alpha$ 1-isopropyl ester, salt of $PGF_2\alpha$ 1-isopropyl ester-15-propione, and 15-deoxy $PGF_2\alpha$ can be given without any limitations. These prostaglandin compounds may be used singularly or in combination of two or more.

Of those given above, prostaglandin $F_2\alpha$ derivatives are preferably used as the prostaglandin compound in the medicine of the present invention, with $PGF_2\alpha$, latanoprost, and isopropyl unoprostone being particularly preferable.

In the medicine of the present invention, the prostaglandin compound is preferably used in an amount of 0.0001-0.05 w/v %, and particular preferably 0.001-0.01 w/v % of the total amount of the medicine.

As the NO donating compound used in the medicine of the present invention, those that release NO (nitric oxide) in vivo can be given. Examples of the NO donating compound include, but are not limited to, nipradilol, nitroglycerine, isosorbide dinitrate, sodium nitroprusside, N-nitrosoacetyl penicillamine, 3-morpholino-sydnonimine hydrochloride, S-nitroso-N-acetyl-DL-penicillamine (SNAP), S-nitrosoglutathione, 4-phenyl-3-furoxanecarbonitryl, arginine, and sodium nitrite. These NO donating compounds may be used singularly or in combination of two or more.

Of the above NO donating compounds, nipradilol is particularly preferable. In addition to releasing NO, nipradilol is known to be effective in $\alpha,\beta$ blocking, which adds an increased effect to the treatment of ocular hypertension and glaucoma.

In the medicine of the present invention, the NO donating compound is preferably used in an amount of 0.01-5 w/v %, and particular preferably 0.1-1.0 w/v % of the total amount of the medicine.

The medicine of the present invention may be used in the form of an eye drop solution and the like, wherein the prostaglandin and NO donating compounds may be combined into a single preparation or each compound may be separate preparations and administered in order in the form of a medicine kit or the like.

In the medicine of the present invention, the use of a single preparation comprising both compounds is advantageous in view of convenience. On the other hand, the use of each compound in separate preparations is also advantageous because the method of administration can be determined and the amount of each compound administered can be controlled.

The medicine of the present invention is preferably used in the form of an eye drop solution. This eye drop solution may comprise the prostaglandin compound and the NO donating compound in separate containers or both the prostaglandin compound and NO donating compound in the same container.

In the preparation of the above medicine, commonly used base materials, dissolution agents, solubilizers, solvents, wetting agents, emulsifiers, excipient, adhesives, viscous agents, binders, preservatives, antioxidants, stabilizers, surfactants, antiseptics, pH adjustors, and the like may be appropriately used in accordance with the form of the preparation.

EXAMPLES

The present invention will be described in more detail by the way of examples, which should not be construed as limiting the present invention.

Example 1

100 ml of an aqueous solution containing 0.25 w/v % of nipradilol and 100 ml of an aqueous solution containing 0.005 w/v % of latanoprost were prepared separately and combined into a single package to prepare a medicine kit.

Example 2

100 ml of an aqueous solution containing 0.1 w/v % of sodium nitroprusside and 100 ml of an aqueous solution containing 0.005 w/v % of latanoprost were prepared separately and combined into a single package to prepare a medicine kit.

Examples 3 and 4

The medicines of Examples 3 and 4 were prepared using the ingredients and amounts shown in Table 1.

TABLE 1

| | Example 3 | | Example 4 | |
|---|---|---|---|---|
| nipradilol | 0.25 g | | nitroprusside Na | 0.10 g |
| latanoprost | 0.005 g | | latanoprost | 0.005 g |
| purified water | appropriate amount | | purified water | appropriate amount |
| total amount | 100 mL | | total amount | 100 mL |

Test Example 1

Domesticated rabbits intravenously administered with 100 μl of a 5 w/v % hypertonic saline solution were used as ocular hypertension models. After intravenously administering the hypertonic saline solution, 50 μl of each of the eye drop solutions were administered and the ocular tension was measured 60 and 120 minutes thereafter.

A physiological saline solution, a 0.005 w/v % latanoprost aqueous solution (latanoprost), a 0.25 w/v % nipradilol aqueous solution (nipradilol), a combination of latanoprost and nipradilol (Example 1), and a combination of a 0.5 w/v % indomethacin aqueous solution (indomethacin), latanoprost, and nipradilol were used as the eye drop solutions.

When nipradilol and latanoprost were used in combination, nipradilol was administered first and latanoprost was administered five minutes thereafter. Furthermore, when indomethacin was used, the indomethacin was administered five minutes before the administration of nipradilol. The results are shown in Table 2, wherein the ocular tension change (mmHg), the change in ocular tension after administration, is shown as the mean value±the standard error.

TABLE 2

| | No. of | Ocular tension change (mmHg) | |
|---|---|---|---|
| Eye drop solution | specimens | 60 minutes | 120 minutes |
| Physiological saline solution | 6 | 24.8 ± 1.7 | 16.2 ± 1.6 |
| Latanoprost | 6 | 22.7 ± 1.2 | 9.8 ± 1.9 |
| Nipradilol | 6 | 14.7 ± 1.7* | 7.3 ± 1.6* |
| Nipradilol + Latanoprost (Example 1) | 6 | 5.3 ± 3.3***[a,b] | 1.7 ± 2.7**[a] |
| Indomethacin + Nipradilol + Latanoprost | 6 | 13.3 ± 3.7*[a] | 8.2 ± 1.7* |

*$p < 0.05$,
**$p < 0.01$ (Dunnett's multiple comparison test, comparison with physiological saline solution)
[a]$p < 0.05$,
[a]$p < 0.01$ (Dunnett's multiple comparison test, comparison with latanoprost solution)
[b]$p < 0.05$ (Dunnett's multiple comparison test, comparison with nipradilol)

Test Example 2

Domesticated rabbits intravitreously administered with 100 μl of a 5 w/v % hypertonic saline solution were used as ocular hypertension models. After intravitreously administering the hypertonic saline solution, 50 μl of each of the eye drop solutions was administered, and the ocular tension was measured 60 and 120 minutes thereafter.

A 0.1 w/v % sodium nitroprusside aqueous solution (sodium nitroprusside), a combination of the sodium nitroprusside and a 0.005 w/v % latanoprost aqueous solution (latanoprost) (Example 2) and a combination of a 0.5 w/v % indomethacin aqueous solution (indomethacin), latanoprost, and sodium nitroprusside were used as the eye drop solutions.

When sodium nitroprusside and latanoprost were used in combination, sodium nitroprusside was administered first and latanoprost was administered five minutes thereafter. Furthermore, when indomethacin was used, the indomethacin was administered five minutes before administration of sodium nitroprusside. The results are shown in Table 3, wherein the ocular tension reduction (mmHg), the change in ocular tension after administration, is shown as the mean value±the standard error.

TABLE 3

| Eye drop solution | No. of specimens | Ocular tension reduction (mmHg) | |
|---|---|---|---|
| | | 60 minutes | 120 minutes |
| Sodium nitroprusside | 5 | 18.0 ± 2.4 | 9.4 ± 2.5 |
| Sodium nitroprusside + latanoprost (Example 2) | 5 | 4.8 ± 3.9 | −2.8 ± 1.3** |
| Indomethacin + sodium nitroprusside + latanoprost | 5 | 22.8 ± 2.9## | 12.4 ± 6.3## |

**$p < 0.01$ (Dunnett's multiple comparison test, comparison with sodium nitroprusside)
$p < 0.01$ (Dunnett's multiple comparison test, comparison with sodium nitroprusside + latanoprost solution)

The results of the above Test Examples 1 and 2 show that the combination of the NO donating compound and prostaglandin compound significantly suppresses an increase in ocular tension when compared with the case where these compounds are individually used. The effect of this combination disappeared with the addition of indomethacin. This suggests that the effect of preventing an increase in ocular tension possessed by the combination of the NO donating compound and latanoprost is a result of cycloxygenase activation. The strengthened production of various endogenic prostaglandins resulting from a synergistic effect of the endogenic arachidonic acid derivative produced by the activation of phospholipase A2 by latanoprost and the activation of cycloxygenase by NO is believed to have stimulated production of $PGE_2$, which is known to be effective for ocular tension reduction in domesticated rabbits.

INDUSTRIAL APPLICABILITY

A medicine comprising a combination of a prostaglandin compound and NO donating compound significantly suppresses an increase in ocular tension when compared to the compounds used individually.

Therefore, the medicine of the present invention is effective in treating persons affected by ocular hypertension and glaucoma.

The invention claimed is:

1. A composition comprising:
   latanoprost, and
   at least one NO-donating compound.
2. The composition of claim 1, wherein the at least one NO-donating compound is selected from the group consisting of nitroglycerine, isosorbide dinitrate, N-nitrosoacetyl penicillamine, 3-morpholine-sydnonimine hydrochloride, S-nitroso-N-acetyl-DL-penicillamine (SNAP), S-nitrosoglutathione, 4-phenyl-3-furoxanecarbonitryl, arginine, and sodium nitrite.
3. The composition of claim 1 which comprises latanoprost and nipradilol.
4. The composition of claim 1 which comprises latanoprost and sodium nitroprusside.
5. The composition of claim 1, further comprising at least one ingredient selected from the group consisting of a base material, a dissolution agent, a solublizer, a solvent, a wetting agent, an emulsifier, an excipient, an adhesive, a viscous agent, a binder, a preservative, an antioxidant, a stabilizer, a surfactant, an antiseptic, and a pH adjuster.
6. The composition of claim 1 in the form of an eye drop.
7. The composition of claim 1, wherein the lantanoprost is present in a concentration ranging from 0.001-0.01 w/v %.
8. The composition of claim 1, wherein the at least one NO-donating compound is present in a concentration ranging from 0.1-1.0 w/v %.
9. A kit comprising:
   packaging material, and
   the composition of claim 1.
10. A kit comprising:
    a packaging material,
    a separate container containing lantanoprost or a lantanoprost composition and
    a separate container containing a NO-donating compound or a NO-donating compound composition.

* * * * *